United States Patent [19]
Horn

[11] Patent Number: 5,256,661
[45] Date of Patent: Oct. 26, 1993

[54] SUBSTITUTED 2-AMINOTETRALINS AND PHARMACEUTICAL USE

[75] Inventor: Alan S. Horn, AW Groningen, Netherlands

[73] Assignee: Whitby Research, Inc., Richmond, Va.

[21] Appl. No.: 951,993

[22] Filed: Sep. 28, 1992

Related U.S. Application Data

[60] Division of Ser. No. 757,336, Sep. 10, 1991, Pat. No. 5,177,112, which is a continuation of Ser. No. 371,207, Jun. 26, 1989, abandoned, which is a continuation-in-part of Ser. No. 891,223, Jul. 28, 1986, abandoned, which is a continuation-in-part of Ser. No. 811,768, Dec. 20, 1985, Pat. No. 4,657,925, which is a continuation-in-part of Ser. No. 640,685, Aug. 13, 1984, Pat. No. 4,564,628, which is a continuation-in-part of Ser. No. 455,144, Jan. 3, 1983, abandoned, said Ser. No. 891,223, is a continuation-in-part of Ser. No. 839,976, Mar. 17, 1986, Pat. No. 4,722,933, which is a continuation-in-part of Ser. No. 640,685, Aug. 13, 1984, Pat. No. 4,564,628, which is a continuation-in-part of Ser. No. 455,144, Jan. 3, 1983, abandoned.

[51] Int. Cl.$^5$ .............. A61K 43/08; A61K 43/10; A61K 43/38; A61K 43/42

[52] U.S. Cl. .................. 514/248; 514/249; 514/259; 514/261; 514/299; 514/300; 514/306; 514/311; 514/359; 514/364; 514/367; 514/375; 514/406; 514/415; 514/443; 514/456; 514/469; 544/235; 544/237; 544/277; 544/283; 544/353; 546/112; 546/117; 546/122; 546/138; 546/174; 546/176; 548/126; 548/152; 548/179; 548/180; 548/217; 548/257; 548/260; 548/261; 548/362.5; 548/504; 549/43; 549/49; 549/58; 549/407; 549/467

[58] Field of Search .......... 544/235, 237, 277, 283, 544/353; 546/112, 117, 122, 138, 174, 176; 548/126, 152, 179, 180, 217, 257, 260, 261, 362.5, 504; 549/43, 49, 58, 407, 467; 514/248, 249, 259, 261, 299, 300, 306, 311, 359, 364, 367, 375, 406, 415, 443, 456, 469

[56] References Cited

U.S. PATENT DOCUMENTS

| | | | |
|---|---|---|---|
| 4,564,628 | 1/1986 | Horn | 514/438 |
| 4,657,925 | 4/1987 | Horn | 514/438 |
| 4,722,933 | 2/1988 | Horn | 514/438 |
| 4,743,618 | 5/1988 | Horn | 514/438 |
| 4,882,352 | 11/1989 | Horn | 514/415 |
| 4,996,226 | 2/1991 | Horn | 514/438 |

*Primary Examiner*—Richard L. Raymond
*Attorney, Agent, or Firm*—Richard J. Hammond

[57] ABSTRACT

Certain novel compounds having the structural formula

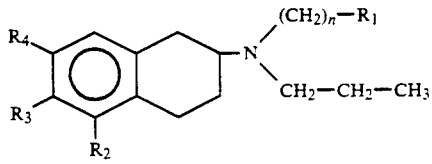

where $R_2$, $R_3$ and $R_4$ are each selected from the group consisting of H and OA; A is H or is selected from the group consisting of hydrocarbyl radicals, e.g. lower alkyl radicals, i.e. methyl, ethyl, propyl, etc., or

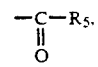

wherein $R_5$ is selected from the group consisting of hydrocarbyl radicals, e.g. alkyl and aromatic residues; n is 2 or 3; and $R_1$ is selected from the group consisting of organic radicals having fused aromatic rings, that is, radicals comprising at least two rings that share a pair of carbon atoms or share a carbon and nitrogen atom are useful for inducing a dopaminergic response and reducing the intraocular pressure in a mammal.

19 Claims, No Drawings

SUBSTITUTED 2-AMINOTETRALINS AND PHARMACEUTICAL USE

CROSS REFERENCE TO RELATED APPLICATIONS

This is a divisional of application Ser. No. 07/757,336, filed Sep. 10, 1991, now U.S. Pat. No. 5,177,112, which is a continuation of application Ser. No. 07/371,207, filed Jun. 26, 1989, now abandoned, which is a continuation-in-part of U.S. patent application Ser. No. 891,223, filed on Jul. 28, 1986, now abandoned which is a continuation-in-part of U.S. patent application Ser. No. 811,768, filed on Dec. 20, 1985, now U.S. Pat. No. 4,657,925, which is a continuation-in-part of U.S. patent application Ser. No. 640,685, filed on Aug. 13, 1984, now U.S. Pat. No. 4,564,628, which is a continuation-in-part of U.S. patent application Ser. No. 455,144, filed Jan. 3, 1983 and now abandoned. Patent application Ser. No. 891,223 is also a continuation-in-part of U.S. patent application Ser. No. 839,976, which was filed on Mar. 17, 1986, now U.S. Pat. No. 4,722,933, which is a continuation-in-part of U.S. patent application Ser. No. 640,685, filed on Aug. 13, 1984, now U.S. Pat. No. 4,564,628, which is a continuation-in-part of U.S. patent application Ser. No. 455,144, filed Jan. 3, 1983 and now abandoned. All of the above applications were filed in the name of Alan S. Horn and are hereby incorporated by reference.

BACKGROUND OF THE INVENTION

1. Field of the Invention

The invention relates generally to substituted 2-aminotetralins and to processes for preparing such compounds. More particularly, the invention relates to compounds for therapeutic use, in particular in treating disorders of the central nervous, cardiovascular and endocrine systems. The compounds of this invention are also useful for alleviating glaucoma in mammals.

2. Background of the Prior Art

It is known that various hydroxylated 2-aminotetralins of the general formula

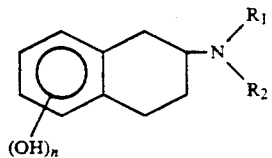

where $R_1$ and $R_2$ are saturated alkyl groups and n is 1 or 2, are dopamine receptor agonists (McDermed et al., J. Med. Chem. 18, 362 (1975); Feenstra et al., Arch. Pharmacol. 313, 213 (1980).

It is also known that certain dopaminergic compounds can lower intraocular pressure in various mammals. For example, it has been suggested that bromocriptine may lower intraocular pressure in man. (See The Lancet, Feb. 4, 1984, "Bromocriptine Eyedrops Lower Intraocular Pressure without Affecting Prolactin Levels.", by Mekki, et al. at pages 287-288.)

Similarly, bromocriptine, as well as lergotrile and pergolide has been shown to lower the intraocular pressure of rabbits and the latter two compounds also lowered the intraocular pressure of monkeys. (see Potter, D.E. and Burke, J.A. (1982/1983), "Effects of Ergoline Derivatives on Intraocular Pressure and Iris Function in Rabbits and Monkeys", Curr. Eye res. 2, 281-288 and Potter, D.E., Burke, J.A. and Chang, F.W. (1984), "Ocular Hypotensive Action of Ergoline Derivatives in Rabbits: Effects of Sympathectomy and Domperidone Pretreatment", Curr. Eye Res. 3, 307-314.)

It has also been shown that certain dopamine analogs of the phenylethylamine class, e.9. N-methyldopamine, N,N-dimethyl-dopamine and N,N-di-n-propyldopamine, may alter ocular function by operating through a variety of mechanisms. However, N-methyl dopamine appeared to function by suppressing aqueous humor formation. (See Potter, D.E., Burke, J.A. and Chang, F.W. (1984), "Alteration in Ocular Function Induced by Phenylethylamine Analogs of Dopamine", Curr. Eye Res. 3, 851-859.)

Finally, certain aminotetralins were shown to lower intraocular pressure in rabbits. (See Burke, J.A., Chang., F.W. and Potter, D.E. (1984), "Effects of Aminotetralins on Intraocular Pressure and Pupillary Function in Rabbits", J. Auton, Pharmacol. 4, 185–192.)

SUMMARY OF THE INVENTION

There has now been discovered certain novel compounds having the structural formula

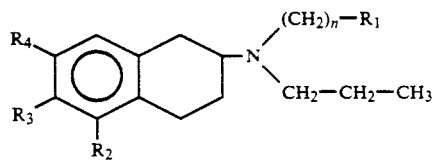

where $R_2$, $R_3$ and $R_4$ are each selected from the group consisting of H and OA; A is H or is selected from the group consisting of hydrocarbyl radicals, e.g. lower alkyl radicals, i.e. methyl, ethyl, propyl, etc., or

wherein $R_5$ is selected from the group consisting of hydrocarbyl radicals, e.g. alkyl and aromatic residues; n is 2 or 3; and $R_1$ is selected from the group consisting of organic radicals having fused aromatic rings, that is, radicals comprising at least two rings that share a pair of carbon atoms or a carbon and nitrogen atom. Preferably $R_1$ comprises no more than 3 fused aromatic rings, and more preferably $R_1$ comprises 2 fused aromatic rings. Examples of radicals suitable for $R_1$ include naphthyl, anthracyl, phenanthryl, benzofuranyl, benzothienyl, indolyl, indazolyl, benzotriazolyl, triazolopyridinyl, benzoxazolyl, benzothiazolyl, benzoxadiazolyl, benzopyranyl, quinolyl, phthalazinyl, purinyl, naphthothienyl, indolizinyl, quinolizinyl, naphthyridinyl, quinoxalinyl, quinazolinyl, cinnolinyl, etc. The above radicals may also be substituted with various functional groups. In particular, such substituents may be selected from the group consisting of hydroxy, nitro, azido, sulfonamido, halogen, hydrocarbyl and hetero atom-substituted hydrocarbyl radicals, wherein said hetero-atoms are selected from the group consisting of halogen, nitrogen, oxygen, sulfur and phosphorus and said hydrocarbyl radicals comprise from 1 to 12 carbon atoms. In the compounds of the present invention, at least one of $R_2$, $R_3$ and $R_4$ is H, and at least one of $R_2$, $R_3$ and $R_4$ is not H, and $R_2$ and $R_4$ are not both OA.

These compounds are useful as dopamine agonists and, in particular, dopamine D-2 receptor agonists for the treatment of disorders of the central nervous, cardiovascular and endocrine systems such as Parkinson's disease and related disorders, hypertension and hyperprolactinemia. In particular, the compounds of this invention are useful in the treatment of glaucoma in mammals.

DETAILED DESCRIPTION OF THE INVENTION

The above compounds may be made by any of the methods disclosed in the patent applications cited above and incorporated by reference herein.

Preferably $R_1$ is selected from the group of radicals represented by the general formulae:

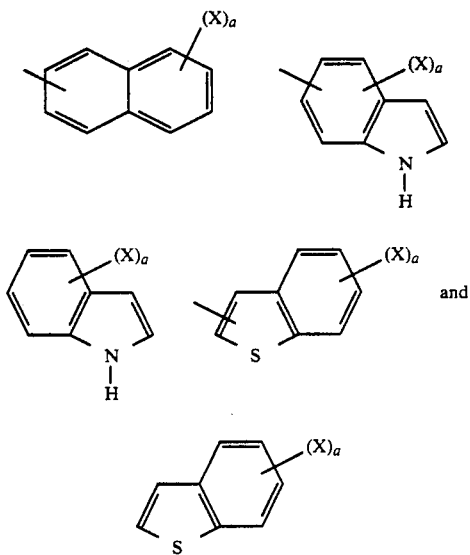

wherein X is selected from the group consisting of hydroxy, alkoxy, nitro, cyano, azido, amino, trifluoromethyl, alkylamino, dialkylamino, halo, carboxyl, carbalkoxy, alkyl, alkenyl, alkynyl, cycloalkyl, aryl, acylamino, carboxamido, sulfonamido, and $SO_m$-(lower)alkyl, wherein m is 0, 1 or 2 and a is an integer of from 0 to 3. More preferably, X comprises no more than 5 carbon atoms and a is 0 or 1. Specific preferred compounds, which are within the scope of the above general formula include:

2-(N-n-propyl-N-2-[naphthalene]ethylamino)-5-hydroxytetralin 2-(N-n-propyl-N-2-[4-indolyl]ethylamino)-5-hydroxytetralin.

2-(N-n-propyl-N-2-[benzothienyl]ethylamino)-5-hydroxytetralin.

2-(N-n-propyl-N-3-[benzothienyl]ethylamino)-5-hydroxytetralin.

A preferred embodiment of this invention is a method of treatment which comprises inducing a dopaminergic response by administering a therapeutically effective amount of one of the foregoing compounds to a patient. In general, a pharmacologically effective daily dose can be from 0.01 mg/kg to 100 mg/kg per day, and preferably from about 0.1 mg/kg to 25 mg/kg per day, bearing in mind, of course, that in selecting the appropriate dosage in any specific case, consideration must be given to the patient's weight, general health, metabolism, age and other factors which influence response to the drug. A particularly preferred dose is 1.0 mg/kg per day.

Another embodiment of this invention is the provision of pharmaceutical compositions in dosage unit form which comprise from about 2 mg. to 500 mg. of a compound of the above formula.

The pharmaceutical composition may be in a form suitable for oral use, for example, as tablets, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents, and preserving agents in order to provide a pharmaceutically elegant and palatable preparation. Tablets contain the active ingredient in admixture with non-toxic pharmaceutically acceptable excipients which are suitable for manufacture of tablets. These excipients may be, for example, inert diluents, for example calcium carbonate, sodium carbonate, lactose, calcium phosphate, or sodium phosphate; granulating and disintegrating agents, for example maize starch, or alginic acid; binding agent, for example starch, gelatine, or acacia; and lubricating agents, for example magnesium stearate, stearic acids, or talc. The tablets may be uncoated or they may be coated by known techniques to delay disintegration and adsorption in the gastrointestinal tract and thereby provide a sustained action over a longer period.

Formulations for oral use may also be presented as hard gelatine capsules wherein the active ingredient is mixed with an inert solid diluent, for example calcium carbonate, calcium phosphate, or kaolin, or as soft gelatine capsules wherein the active ingredient is mixed with an oil medium, for example arachis oil, liquid paraffin, or olive oil.

Aqueous suspensions contain the active compound in admixture with excipients suitable for the manufacture of aqueous suspensions Such excipients are suspending agents, for example sodium carboxymethylcellulose, methylcellulose, hydroxypropylmethylcellulose, sodium alginate, polyvinylpyrrolidone, gum trangacanth, and gum acacia; dispersing or wetting agents may be a naturally-occurring phosphatide, for example lecithin, or condensation products of an alkylene oxide with fatty acids, for example of polyoxethylene stearate, or condensation products of ethylene oxide with long chain aliphatic alcohols, for example heptadecaethyleneoxycetanol, or condensation products of ethylene oxide with partial esters derived from fatty acids and a hexitol, for example, polyoxyethylene sorbitol monooleate, or condensation product of ethylene oxide with partial esters derived from fatty acids and hexitol anhydrides, for example polyoxyethylene sorbitan monooleate. The said aqueous suspensions may also contain one or more preservatives, for example ethyl, n-propyl, or p-hydroxy benzoate, one or more coloring agents, one or more flavoring agents, and one or more sweetening agents, such as sucrose, saccharin, or sodium or calcium cyclamate.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents, may also be present.

Syrups and elixirs may be formulated with sweetening agents, for example glycerol, sorbitol or sucrose. Such formulations may also contain a demulcent, a preservative and flavoring and coloring agents. The pharmaceutical compositions may be in the form of a sterile injectable preparation, for example as a sterile injectable aqueous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol.

The pharmaceutical compositions may be tableted or otherwise formulated so that for every 100 parts by weight of the composition there are present between 5 and 95 parts by weight of the active ingredient. The dosage unit form will generally contain between about 1 mg. and about 100 mg. of the active ingredient of the formula stated above.

From the foregoing formulation discussion it is apparent that the compositions of this invention can be administered orally or parenterally. The term parenteral as used herein includes subcutaneous injection, intraveneous, intramuscular, or intrasternal injection or fusion techniques.

Even more preferably, the method of the present invention comprises administering the above-described compounds to the eye of a mammal to reduce intraocular pressure. Moreover, the levo (−) isomers of these substituted compounds are believed to be the more active isomers for use in the method of the present invention.

Suitable ophthalmic carriers are known to those skilled in the art and all such conventional carriers may be employed in the present invention. Thus, a particular carrier may take the form of a sterile ophthalmic cointment, cream, gel, solution, or dispersion and preferably a solution. Also including as suitable ophthalmic carriers are slow releasing polymers, e.g. "Ocusert" polymers, "Hydron" polymers, etc. Stabilizers may also be used as, for example, chelating agents,, e.g. EDTA. Anti-oxidants may also be used, e.g. sodium bisulfite, sodium thiosulfite, 8-hydroxy quinoline or ascorbic acid. Sterility typically will be maintained by conventional ophthalmic preservatives, e.g. chlorbutanol, benzalkonium chloride, cetylpyridinium chloride, phenyl mercuric salts, thimerosal, phenethyl alcohol, etc., for aqueous formulations, and used in amounts which are nontoxic and which generally vary from about 0.001 to about 0.1% by weight of the aqueous solution. Conventional preservatives for ointments include methyl and propyl parabens. Typical ointment bases include white petrolatum and mineral oil or liquid petrolatum. However, preserved aqueous carriers are preferred. Solutions may be manually delivered to the eye in suitable dosage form, e.g., eye drops, or delivered by suitable microdrop or spray apparatus typically affording a metered dose of medicament. Examples of suitable ophthalmic carriers or stabilizers include sterile, substantially isotonic, aqueous solutions containing minor amounts, i.e., less than about 5% by weight hydroxypropylmethylcellulose, polyvinyl alcohol, carboxymethylcellulose, hydroxyethylcellulose, glycerine, EDTA, sodium bisulfite and ascorbic acid.

The amount of active compound to be used in the therapeutic treatment of glaucoma will vary with the age of the patient and the severity of the glaucoma. Generally, a dose level of one or two drops of the foregoing aqueous solution 1–4 times daily would be a suitable dosage amount. Generally, the concentration of active compound will vary between about 0.01 and about 5% and preferably between about 0.05 and about 1%% (wt./v calculated on the basis of the free base) of said ophthalmic composition.

Preferably, the ophthalmic composition of this invention should have a pH within the range of about 4.0 to 9.0 when intended for topical application. Above and below this pH range the solution may irritate and sting the eye of the user. The solutions of the present invention may be maintained between about pH 4.0 and 7.5 with suitable amounts of buffering agents including borate, carbonate, phosphate. Tris (hydroxymethyl aminomethane), acetate and citrate buffers.

A preferred ophthalmic composition is a preserved aqueous solution containing the following ingredients at approximately the indicated concentration.

TABLE

| | |
|---|---|
| Active compound | 0.001–1 wt. % |
| Stabilizer | 0.01–0.1 wt. % |
| Preservative | 0.005–0.5 wt. % |
| Buffer (sufficient to maintain pH between about 4.0 and 7.5) | 0.1–0.001M |
| NaCl qs. ad. | (isotonic) |
| Water qs. ad. | 100% |

To illustrate the manner in which the invention may be carried out, the following examples are given. It is understood, however, that the examples are for the purpose of illustration and the invention is not to be regarded as limited to any of the specific materials or conditions therein.

EXAMPLE 1

Preparation of 2-(N-n-prooyl-N-2-[naphthyl]ethylamino)-5-hydroxytetralin

A mixture of 2-(N-n-propylamino)-5-methoxytetralin, 2-naphthylacetic acid and trimethylaminoborohydride in dry xylene was refluxed under an atmosphere of nitrogen as described by Horn et al. Pharm. Weekbld. Sci. Ed. 7 208–211, 1985. The resulting methoxy intermediate was demethylated using boron tribromide as described in the above article to yield the desired product.

EXAMPLE 2

Preparation of 2-(N-n-propyl-N-2-[2-benzothienyl]ethylamino)-5-hydroxytetralin

A mixture of 2-(N-n-propylamino)-5-methoxytetralin, 2-benzothienyl acetic acid and trimethylaminoborohydride in dry xylene is refluxed under an atmosphere of nitrogen as described by Horn et al, Pharm. Weekbld. Sci. Ed. 7 208–211, 1985. The resulting methoxy intermediate is demethylated using boron tribromide as described in the above article to yield the desired product.

EXAMPLE 3

Preparation of 2-(N-n-propyl-N-2-[4-indolyl]ethylamino)-5-hydroxytetralin

The procedure of Example 2 is repeated substituting 4-indolylacetic acid for 2-benzothienylacetic acid to obtain the corresponding methoxy intermdiate. This intermediate is also demethylated by the procedure described in the Horn article to yield the desired product.

EXAMPLE 4

The pharmacological activity of the product of Example 2 was determined by examining its ability to displace the specific D-2 dopamine receptor binding of a tritium-containing racemic mixture of 2-(N-propyl-N-2-thienylethylamino)-5-hydroxytetralin to homogenates of calf brain corpus striatum. In this preparation, which is a modification of the one reported by Mulder et al. "Kinetic and Pharmacological Profiles of the In-Vitro Binding of the Potent Dopamine Agonist 3H-N,N-dipropyl-2-Aminotetralin to Rat Striatal Membranes," Eur. J. Pharmacol 112 (1985) 73-79, for rat brain corpus striatum, the tritium-containing racemic mixture had an affinity constant ($K_d$) of 1.6 nanomoles and bmax of 26.0 picomoles/gm. The IC50 values (i.e. the concentration of drug required to inhibit the binding of labelled drug by 50 percent for the product of Example 2 was 0.56 nanomoles.

The activity at the D-1 dopamine receptor was tested by the method described in Raisman et al. *Eur. J. Pharmacol 113*: (1985), pp. 467-468, which utilizeds membranes isolated from the striatum of bovine brain. In this preparation the compound of Example 2, over a concentration range of from to $10^{-11}$-$10^{-4}$ moles did not displace the tritium labeled SCH 23390 compound, a known, selective D-1 antagonist. Thus, the $1C_{50}$ value for the compound of Example 2 is >100,000 at the D-1 receptor. The compound of Example 2 thus shows extremely selective D-2 as opposed to D-1 binding, in contrast to dopamine and apomophine which show a substantially equivalent binding at the D-1 and D-2 receptor.

EXAMPLE 5

Dopamine receptor assays: Specific binding studies to test the affinity of the compounds for $D_1$, $D_2$ and $\alpha_2$ receptors were conducted using bovine caudate nuclei prepared as follows:

Bovine brains were obtained fresh from a local slaughterhouse. The caudate nuclei were dissected out and homogenized in Buffer A (50 mM Tris; 1 mM $Na_2$-EDTA; 5 mM KCl; mM $MgCl_2$; 2 mM $CaCl_2$; pH 7.4) using a Brinkman Polytron. The homogenate was centrifuged at 40,000 x g for 20 minutes and washed once. The pellett was resuspended in Buffer A, incubated at 37° C. for 15 minutes, then centrifuged. The pellet was washed once more, resuspended to a protein concentration of 5-10 mg/ml in Buffer A and frozen at -70° C. until used.

$\alpha_2$-adrenergic receptors assays were conducted using the rat cerebral cortex prepared as follows:

Male Sprague Dawley rats were killed by decapitation and the brains removed. The cerebral cortices were homogenized in 50 mM Tris; 2mM $MgCl_2$ (pH 7.4), and centrifuged at 40,000×g for 10 minutes. The pellet was washed once, resuspended in Tris/$MgCl_2$ and incubated with 8 units/ml adenosine deaminase at 37° C. for 30 minutes. The homogenate was centrifuged, washed once, resuspended to a protein concentration of 5-10 mg/ml and frozen at -70° C. until use.

The following tritiated drugs were used as radioligands in the binding studies:

[$^3$H]-Spiperone 21-24 Ci/mmol for $D_2$ receptors
[$^3$H]-SCH23390 75-85 Ci/mmol for $D_1$ receptors
[$^3$H]-Para aminoclonidine 48-52 Ci/mmol for $\alpha_2$-adrenergic receptors.

[$^3$H]-spiperone, [$^3$H]-SCH22390, and [$^3$H]-ketanserin were obtained from New England Nuclear, Boston, Mass.

[$^3$H]-paraaminoclonidine was obtained from Amersham, Arlington Heights, Ill. Yohimbine was obtained from Sigma Chemical Co., St. Louis. Mo.

The radioligands were incubated with various concentrations of competing drug and the appropriate membrane source for 75 minutes at room temperature for $D_2$ receptors, 15 minutes at 37° C. for $D_1$ receptors, or 30 minutes at room temperature for $\alpha_2$ receptors. Specific binding was defined using 1μM butaclamol ($D_2$), 1 μM SCH23390 ($D_1$), or 1 μM yohimbine ($\alpha_2$). In addition the $D_2$ assays contained 30 nM ketaserin in order to block the binding of $^3$H-spiperone to $5HT_2$ receptors. The assays were terminated by filtration using a 24-port Brandell cell harvester over filters that had been previously soaked in 0.1% polyetheleneimine, and the filters were washed three times by filtration of cold buffer. The filters were then placed in 5 ml scintillation vials to which 4 ml of Beckman Ready-Protein was then added, and each vial was counted for 2 minutes in a Beckman 3801 scintillation counter calibrated for conversion of cpm to dpm. Binding data were analyzed using the Ligand program of Munson and Rodbard (1980). The results are presented as $K_i$ values if the data were best fitted to a one-site model, or as $K_H$ and $K_L$ values if a two-site model produced the better fit.

The results of the specific binding tests are summarized below in Table 1:

TABLE 1

SPECIFICITY AND SELECTIVITY OF FUSED RING N-SUBSTITUTED 2-AMINOTETRALINS

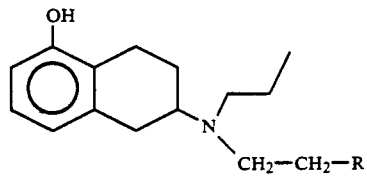

| R | $K_i$ (nM) | | |
|---|---|---|---|
| | $D_2$ | $D_1$ | $\alpha_2$ |
| 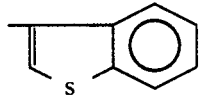 | 110 | 1,000 | 190 |
| 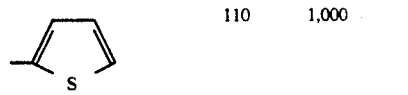 | 130 | 1,950 | 250 |

TABLE 1-continued
SPECIFICITY AND SELECTIVITY OF FUSED RING
N-SUBSTITUTED 2-AMINOTETRALINS

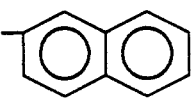

| R | $K_i$ (nM) | | |
|---|---|---|---|
| | $D_2$ | $D_1$ | $\alpha_2$ |
| 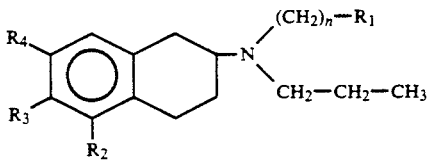 | 80 | 6,460 | 2,500 |

Compared to the compound having R as a single ring compound (thienyl), the fused ring compounds (benzothienyl and napthyl substituted compounds) exhibit respectively roughly a two-fold and six and a half-fold increase in selectivity for $D_2$ receptors. The specificity of the fused ring compounds for dopamine receptors over $\alpha_2$ receptors is also increased over that exhibited by the thienyl-substituted compound.

While particular embodiments of the invention have been described it will be understood, of course, that the invention is not limited thereby since many obvious modifications can be made and it is intended to include within this invention any such modifications as will fall within the scope of the appended claims.

What is claimed is:

1. Optically active or racemic compounds having the general formula:

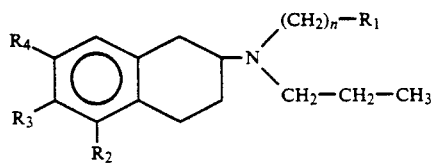

wherein $R_2$, $R_3$ and $R_4$ are each selected from the group consisting of H and OA; A is selected from the group consisting of hydrogen, hydrocarbyl radicals, and radicals represented by the general formula —C(O)—$R_5$, wherein $R_5$ is selected from the group consisting of hydrocarbyl radicals, n is 2 or 3 and $R_1$ is selected from the group consisting of benzofuranyl, indazolyl, benzotriazolyl, triazolopyridinyl, benzoxazolyl, benzothiazolyl, benzoxadiazolyl, benzopyranyl, quinolyl, phthalazinyl, purinyl, naphthothienyl, indolizinyl, quinolizinyl, naphthyridinyl, quinoxalinyl, quinazolinyl, cinnolinyl, and substituted derivatives thereof wherein the substituents have no more than 12 carbon atoms and are selected from the group consisting of hydroxy, nitro, azido, sulfonamido, sulfate, halogen, hydrocarbyl and heteroatom-substituted hydrocarbyl wherein said heteroatoms are selected from the group consisting of halogen, nitrogen, sulfur and phosphorus; and wherein at least one of $R_2$, $R_3$ and $R_4$ is H, and at least one of $R_2$, $R_3$ and $R_4$ is not H, and $R_2$ and $R_4$ are not both OA and pharmaceutically-acceptable salts thereof.

2. The compound of claim 1 wherein $R_2$, $R_3$ and $R_4$ are selected from the group consisting of hydrogen and

3. The compound of claim 2 wherein $R_5$ is an alkyl or aromatic residue having no more than 20 carbon atoms.

4. The compound of claim 1 wherein $R_4$ and $R_3$ are hydrogen.

5. The compound of claim 4 wherein A is hydrogen.

6. A composition for reducing the intraocular pressure in mammals which comprises an effective amount of a compound selected from the group consisting of compounds having the structural formula:

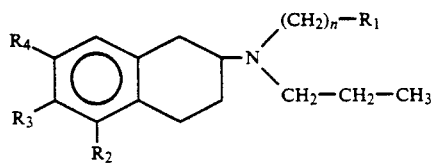

wherein $R_2$, $R_3$ and $R_4$ are each selected from the group consisting of H and OA; A is selected from the group consisting of hydrogen, hydrocarbyl radicals, and radicals represented by the general formula—C(O)—$R_5$, wherein $R_5$ is selected from the group consisting of hydrocarbyl radicals, n is 2 or 3 and $R_1$ is selected from the group consisting of benzofuranyl, indazolyl, benzotriazolyl, triazolopyridinyl, benzoxazolyl, benzothiazolyl, benzoxadiazolyl, benzopyranyl, quinolyl, phthalazinyl, purinyl, naphthothienyl, indolizinyl, quinolizinyl, naphthyridinyl, quinoxalinyl, quinazolinyl, cinnolinyl, and substituted derivatives thereof wherein the substituents have no more than 12 carbon atoms and are selected from the group consisting of hydroxy, nitro, azido, sulfonamido, sulfate, halogen, hydrocarbyl and heteroatom-substituted hydrocarbyl wherein said heteroatoms are selected from the group consisting of halogen, nitrogen, sulfur and phosphorus; and wherein at least one of $R_2$, $R_3$ and $R_4$ is H, and at least one $R_2$, $R_3$ and $R_4$ is not H, and $R_2$ and $R_4$ are not both OA and pharmaceutically acceptable salts thereof, and an ophthalmic carrier for said compound.

7. The composition of claim 6 wherein $R_2$, and $R_3$ and $R_4$ are selected from the group consisting of hydrogen and

8. The composition of claim 7 wherein $R_5$ is an alkyl or aromatic residue having no more than 20 carbon atoms.

9. The composition of claim 6 wherein $R_4$ and $R_3$ are hydrogen.

10. The composition of claim 9 wherein A is hydrogen.

11. A method comprising:
inducing a dopaminergic response in a patient by administering a pharmacologically-effective amount of a compound represented by the general formula:

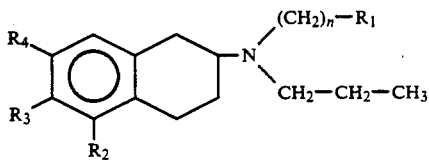

wherein $R_2$, $R_3$ and $R_4$ are each selected from the group consisting of H and OA; A is selected from the group consisting of hydrogen, hydrocarbyl radicals, and radicals represented by the general formula—C(O)—$R_5$, wherein $R_5$ is selected from the group consisting of hydrocarbyl radicals, n is 2 or 3 and $R_1$ is selected from the group consisting of benzofuranyl, indazolyl, benzotriazolyl, triazolopyridinyl, benzoxazolyl, benzothiazolyl, benzoxadiazolyl, benzopyranyl, quinolyl, phthalazinyl, purinyl, naphthothienyl, indolizinyl, quinolizinyl, naphthyridinyl, quinoxalinyl, quinazolinyl, cinnolinyl, and substituted derivatives thereof wherein the substituents have no more than 12 carbon atoms and are selected from the group consisting of hydroxy, nitro, azido, sulfonamido, sulfate, halogen, hydrocarbyl and heteroatom-substituted hydrocarbyl wherein said heteroatoms are selected from the group consisting of halogen, nitrogen, sulfur and phosphorus; and wherein at least one of $R_2$, $R_3$ and $R_4$ is H, and at least one $R_2$, $R_3$ and $R_4$ is not H, and $R_2$ and $R_4$ are not both OA and pharmaceutically-acceptable salts thereof.

12. The method of claim 11 wherein $R_2$, $R_3$ and $R_4$ are selected from the group consisting of hydrogen and

13. The method of claim 12 wherein $R_5$ is an alkyl or aromatic residue having no more than 20 carbon atoms.

14. The method of claim 11 wherein $R_4$ and $R_3$ are hydrogen.

15. The method of claim 14 wherein A is hydrogen.

16. A method for reducing the intraocular pressure in mammals which comprises administering an effective amount of a compound selected from the group consisting of compounds represented by the general formula:

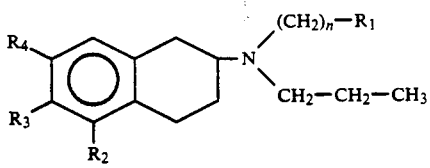

wherein $R_2$, $R_3$ and $R_4$ are each selected from the group consisting of H and OA; A is selected from the group consisting of hydrogen, hydrocarbyl radicals, and radicals represented by the general formula—C(O)—$R_5$, wherein $R_5$ is selected from the group consisting of hydrocarbyl radicals, n is 2 or 3 and $R_1$ is selected from the group consisting of benzofuranyl, indazolyl, benzotriazolyl, triazolopyridinyl, benzoxazolyl, benzothiazolyl, benzoxadiazolyl, benzopyranyl, quinolyl, phthalazinyl, purinyl, naphthothienyl, indolizinyl, quinolizinyl, naphthyridinyl, quinoxalinyl, quinazolinyl, cinnolinyl, and substituted derivatives thereof wherein the substituents have no more than 12 carbon atoms and are selected from the group consisting of hydroxy, nitro, azido, sulfonamido, sulfate, halogen, hydrocarbyl and heteroatom-substituted hydrocarbyl wherein said heteroatoms are selected from the group consisting of halogen, nitrogen, sulfur and phosphorus; and wherein at least one of $R_2$, $R_3$ and $R_4$ is H, and at least one of $R_2$, $R_3$ and $R_4$ is not H, and $R_2$ and $R_4$ are not both OA and pharmaceutically-acceptable salts thereof.

17. The method of claim 16 wherein $R_2$, $R_3$ and $R_4$ are selected from the group consisting of hydrogen and

18. The method of claim 16 wherein $R_4$ and $R_3$ are hydrogen.

19. The method of claim 18 wherein A is hydrogen.

* * * * *